(12) United States Patent
Lee et al.

(10) Patent No.: US 9,709,511 B2
(45) Date of Patent: Jul. 18, 2017

(54) APPARATUS, SYSTEM, METHOD AND COMPUTER-READABLE MEDIUM FOR ISOLATING CHEMICAL EXCHANGE SATURATION TRANSFER CONTRAST FROM MAGNETIZATION TRANSFER ASYMMETRY UNDER TWO-FREQUENCY RF IRRADIATION

(71) Applicant: NEW YORK UNIVERSITY, New York, NY (US)

(72) Inventors: Jae Seung Lee, Corona, NY (US); Ravinder R. Regatte, Monroe, NJ (US); Alexej Jerschow, New York, NY (US)

(73) Assignee: New York University, New York, NY (US)

( * ) Notice: Subject to any disclaimer, the term of this patent is extended or adjusted under 35 U.S.C. 154(b) by 894 days.

(21) Appl. No.: 13/687,342

(22) Filed: Nov. 28, 2012

(65) Prior Publication Data
US 2013/0166226 A1 Jun. 27, 2013

Related U.S. Application Data

(60) Provisional application No. 61/564,016, filed on Nov. 28, 2011.

(51) Int. Cl.
*G01R 33/56* (2006.01)
*G06F 19/00* (2011.01)
*G01N 23/02* (2006.01)

(52) U.S. Cl.
CPC ......... *G01N 23/02* (2013.01); *G01R 33/5605* (2013.01); *G06F 19/707* (2013.01)

(58) Field of Classification Search
CPC .... G01R 33/5605; G06F 19/707; G01N 23/02
See application file for complete search history.

(56) References Cited

U.S. PATENT DOCUMENTS

2007/0134159 A1\* 6/2007 Dixon ............... G01R 33/4804
424/9.3
2008/0021306 A1 1/2008 Van Zijl et al.
(Continued)

FOREIGN PATENT DOCUMENTS

WO WO 2007/014004 A2 2/2007
WO WO2009089274 \* 7/2009 ............ A61B 5/055

OTHER PUBLICATIONS

Zijl et al., "Chemical Exchange Saturation Transfer (CEST): what is in a name and what isn't?", Apr. 2011, Magn Reson Med.; 65(4): 927-948.\*

(Continued)

*Primary Examiner* — Regis Betsch
(74) *Attorney, Agent, or Firm* — Andrews Kurth Kenyon LLP

(57) ABSTRACT

Apparatus, system, method and computer-readable medium for isolating chemical exchange saturation transfer contrast from magnetization transfer asymmetry under two-frequency RF irradiation. A two-pool model for magnetization transfer (MT) can be established fully based on Provotorov's theory of saturation, and then extended to the situation of simultaneous two-frequency RF irradiation. Numerical simulations and experimental results demonstrate that two-frequency RF irradiation can make MT effects independent of irradiation frequency over a wide range, and thus can suppress MT asymmetry. Exemplary embodiments can be provided to isolate chemical exchange saturation transfer (CEST) contrast from MT asymmetry contrast by using the two-frequency RF irradiation technique. A further embodiment can isolate a narrow-frequency spectrum MT mechanism from a broad-frequency spectrum MT mechanism.

37 Claims, 11 Drawing Sheets

(56) References Cited

U.S. PATENT DOCUMENTS

2008/0197840 A1* 8/2008 Van Zijl et al. .............. 324/307
2011/0054299 A1 3/2011 Ling et al.

OTHER PUBLICATIONS

International Search Report for International Patent Application No. PCT/US2012/066832 mail Feb. 19, 2013.

International Written Opinion for International Patent Application No. PCT/US2012/066832 mail Feb. 19, 2013.

Henkelman, R. Mark et al., "Quantitative Interpretation of Magnetization Transfer," MRM, vol. 29, pp. 759-766, 1993.

Goldman, Maurice "Spin Temperature and Nuclear Magnetic Resonance . . .," Oxford at the Clarendon Press, pp. 1-4, 1970.

Zhou, Jinyuan et al., "Chemical Exchange Saturation Transfer Imaging and Spectroscopy," Progress in Nuclear Magnetic Resonance Spectroscopy, vol. 48, pp. 109-136, 2008.

Wolff, Steven D. et al., "Magnetization Transfer Contrast (MTC) and Tissue Water . . .," Magnetic Resonance in Medicine, vol. 10, pp. 135-144, 1989.

Ward, K.M. et al., "A New Class of Contrast Agents for MRI Based on Proton Chemical . . .," Journal of Magnetic Resonance, vol. 143, pp. 79-87, 2000.

Van Zijl, Peter C.M. et al., "Chemical Exchange Saturation Transfer (CEST): . . .," Magn. Reson. Med., vol. 65, No. 4, pp. 927-948, 2011.

Traore, Amidou et al., "1H NMR Studies: Dynamics of Water in Gelatin," Eur Biophys J., vol. 29, pp. 159-164, 2000.

Scheidegger, Rachel et al., "Amide Proton Transfer Imaging with Improved Robustness . . .," Magnetic Resonance in Medicine, vol. 66, pp. 1275-1285, 2011.

Provotorov, B.N. "Magnetic Resonance Saturation in Crystals," Soviet Physics Jetp, vol. 14, No. 6, pp. 1126-1131, May 1962.

Pekar, James et al., "Perfusion Imaging with Compensation for Asymmetric Magnetization Transfer Effects," MRM, vol. 35, pp. 70-79, 1996.

Ling, Wen et al., "Characterization of Bovine Patellar Cartilage by NMR," NMR in Biomedicine, vol. 21, pp. 289-296, 2008.

Ling, Wen et al., "Assessment of Glycosaminoglycan Concentration in vivo by Chemical . . .," PNAS, vol. 105, No. 7, pp. 2266-2270, Feb. 19, 2008.

Levitt, Malcolm H. et al., "Spin Dynamics: Basics of Nuclear Magnetic Resonance," Concepts in Magnetic Resonance Part A, vol. 34A, No. 1, pp. 60-61, 2009.

Leibfritz, Dieter et al., "Magnetization Transfer MRS," NMR Biomedicine, vol. 14, pp. 65-76, 2001.

Lee, Jae-Seung et al., "Uniform Saturation of a Strongly Coupled Sping System . . .," The Journal of Chemical Physics, vol. 134, pp. 234504-1-6, 2011.

Lee, Jae Seung et al., "Thermodynamics of Adiabatic Cross Polarization," The Journal of Chemical Physics, vol. 128, pp. 114504-1-7, 2008.

Lee, Jae-Seung et al., "Pseudopure State of a Twelve-Spin System," The Journal of Chemical Physics, vol. 122, pp. 041101-1-3, 2005.

Hua, Jun et al., "Quantitative Description of the Asymmetry in Magnetization Transfer Effects . . .," Magn. Reson. Med., vol. 58, No. 4, pp. 786-793, Oct. 2007.

Henkelman, R.M. et al., "Magnetization Transfer in MRI: A Review," NMR Biomedicine, vol. 14, pp. 57-64, 2001.

\* cited by examiner

Fig. 4
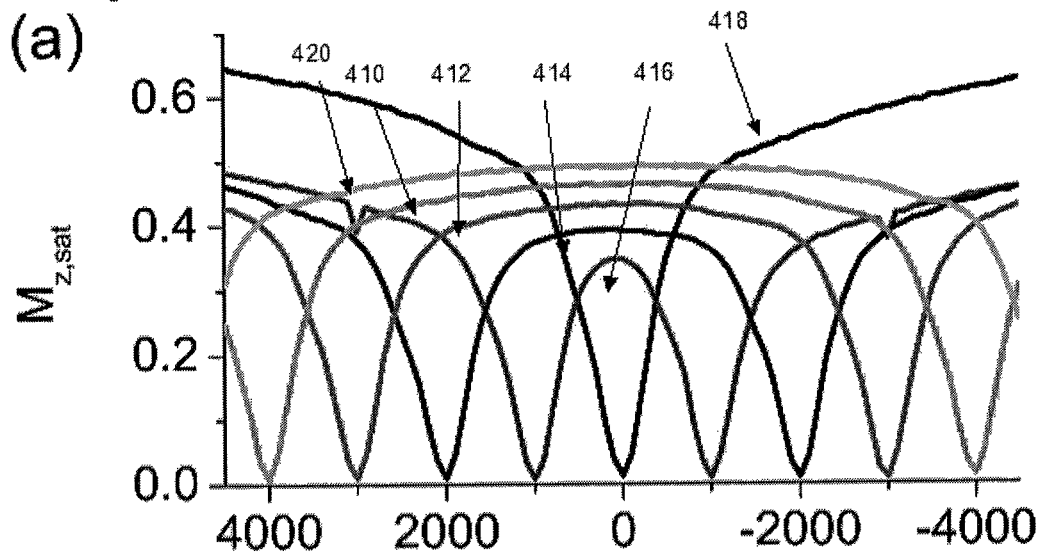
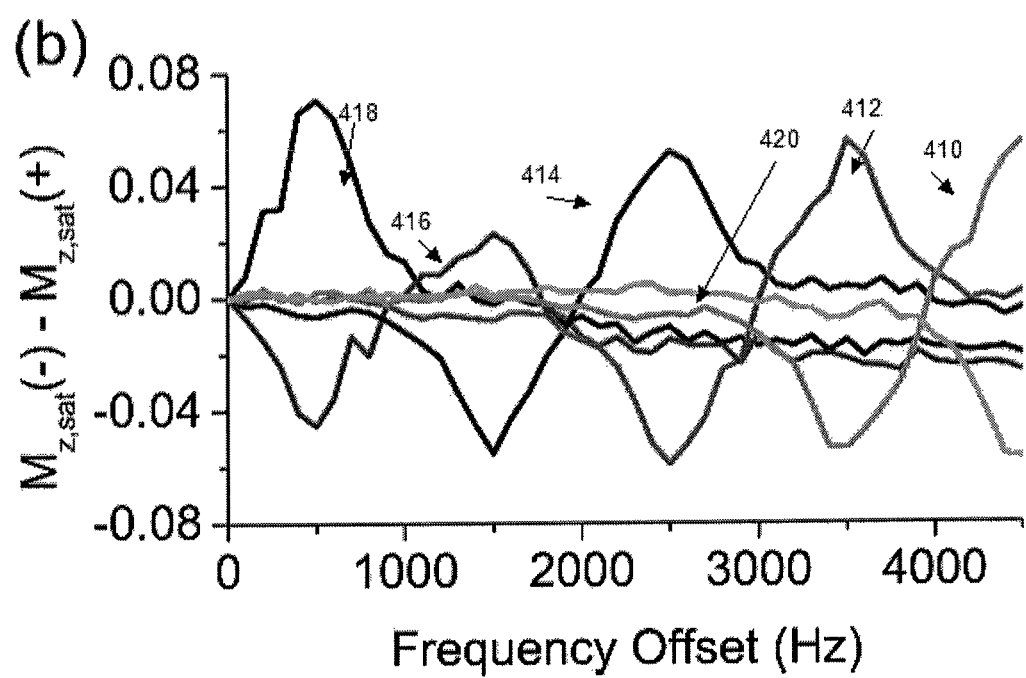

APPARATUS, SYSTEM, METHOD AND COMPUTER-READABLE MEDIUM FOR ISOLATING CHEMICAL EXCHANGE SATURATION TRANSFER CONTRAST FROM MAGNETIZATION TRANSFER ASYMMETRY UNDER TWO-FREQUENCY RF IRRADIATION

CROSS-REFERENCE TO RELATED APPLICATION(S)

This application relates to and claims priority from U.S. Provisional Patent Application No. 61/564,016, filed on Nov. 28, 2011, the entire disclosure of which is incorporated herein by reference in its entirety.

STATEMENT REGARDING FEDERALLY SPONSORED RESEARCH

Portions of the material described herein were funded, at least in part, by National Institute of Health under grant numbers K25AR060269 and R21AR055724, and by National Science Foundation under grant number CHE0957586. Therefore, the Federal Government may have certain rights to the invention.

FIELD OF THE DISCLOSURE

Exemplary embodiments of the present disclosure relate to systems, methods and computer-readable mediums for isolating chemical exchange saturation transfer contrast from magnetization transfer asymmetry under two-frequency radio-frequency ("RF") irradiation.

BACKGROUND INFORMATION

Magnetization transfer ("MT") is, in general, a macroscopic phenomenon in which two distinct pools of nuclear spins exchange their magnetic polarizations. In the field of magnetic resonance imaging ("MRI"), MT can indicate that one of the two pools can consist of water protons, the amount of which is present in large excess in tissues and organs, and the other can consist of protons associated with macromolecules, between which there can exist either a physical exchange or a magnetization exchange via relaxation pathways such as the Nuclear Overhauser Effect ("NOE").

The term chemical exchange saturation transfer ("CEST"), can be caused by chemical exchange, especially between water protons and exchangeable solute protons. In tissues and organs, CEST can occur together with MT, which can make the quantitative measure of CEST difficult. In principle, CEST can be distinguished from conventional MT by its frequency selectivity (e.g., CEST can occur in the very narrow range of frequencies, which can be selectively irradiated and compared with MT happening in a wide range of frequencies). It can be difficult, however, to separate the two effects if an asymmetry in MT exists, which can be very common in biological tissues. Previous work described that one could achieve uniform saturation of a strongly-coupled spin system by simultaneously irradiating at two different frequencies that lie within its dipolar coupling-broadened spectral range. If the MT exchange processes occur on a timescale that is slower than the rate of saturation, the two-frequency radio frequency ("RF") irradiation can uniformly saturate those protons belonging to the macromolecules in tissues and organs. As a result, the magnetization of water protons can diminish through MT exchange processes. Consequently, the MT effect can become independent of the frequency positions of the saturating RF irradiation. Conversely, due to the frequency selectivity of CEST agents, two-frequency RF irradiation does not significantly alter CEST dynamics.

Thus, it may be beneficial to establish a two-pool model for MT based on, for example, Provotorov's theory of saturation and extend the model to describe the dynamics under simultaneous two-frequency irradiation, that can provide an exemplary unencumbered extraction of CEST, and that can overcome at least some of the deficiencies described herein above.

SUMMARY OF EXEMPLARY EMBODIMENTS

Thus, to address at least such needs, certain exemplary embodiments of exemplary architectures, systems, apparatus, methods, and computer-readable medium can be provided to remove magnetization transfer asymmetry. While exemplary embodiments are herein illustrated with the example of CEST isolation and MT asymmetry removal, the exemplary methods can work whenever one mechanism has a narrow frequency spectrum and another mechanism that has a broad frequency spectrum broadened by dipolar coupling. As such, certain exemplary embodiments of the present disclosure can substantially isolate a first transfer in a first frequency spectrum from a second transfer in a second frequency spectrum. Further the first transfer can relate to a first transfer mechanism which can be in a frequency spectrum which is narrower than the second frequency spectrum and can include, e.g., (i) CEST in the case of chemical exchange, or (ii) NOE in the case of through-space magnetization transfer to a small mobile molecule. The second transfer can relate to a second transfer mechanism which can be in a frequency spectrum that is broader than the first frequency spectrum and is broadened by dipolar coupling including, e.g., (A) MT in the case of exchange with a bound state to a macromolecule or (B) magnetization transfer through space to bound moieties on the macromolecule.

Thus, exemplary embodiments of the present disclosure can include illustrative examples using CEST and MT, including determining a first and second distinct frequencies, irradiating a sample with both first and second frequencies, measuring a first residual polarization, determining a third and fourth distinct frequencies, measuring a second residual polarization, and isolating a chemical exchange saturation transfer contrast by subtracting the first measurement from the second measurement.

In the exemplary embodiments of the present disclosure, the first frequency can be based on a resonance frequency of a CEST agent. The second frequency can be outside the typical range of proton chemical shifts, such as more than about 5 parts per million away from a water proton resonance. The second frequency can cause MT effects only, such that protons causing MT experience substantially simultaneous saturation by two frequencies. The third and fourth frequencies can be located symmetrically to the first and second frequencies, respectively, with respect to a water proton resonance frequency. The third and fourth frequencies can be located substantially away from the first and second frequencies. Further, the third and fourth frequencies can be within a range of a spectrum of protons causing MT effects only, such that those protons experience substantially simultaneous saturation by the third and fourth frequencies. The subtracting can eliminate a contribution of direct water saturation, due to a pair-wise symmetric configuration. Also, the subtracting can eliminate an MT contribution because the substantially simultaneous two-frequency irradiation makes MT effects uniform. The exemplary embodiment can also determine additional distinct frequencies, measure additional interactions; and refine the CEST contrast by separating different exchange mechanisms. Another exemplary embodiment of the present disclosure can include exemplary architectures, systems, apparatus, methods, and computer-readable medium to remove magnetization transfer asymmetry and correct magnetic field ($B_0$) inhomogeneity, including determining an $f_1$ frequency and an $f_2$ frequency, defining an $f_d$ as the difference between $f_1$ and $f_2$, defining an $f_0$ as half a sum of $f_1$ and $f_2$, irradiating a sample with a first frequency equal to $f_0$ less half of $f_d$, simultaneously irradiating the sample with a second frequency equal to $f_0$ plus half of $f_d$; and measuring a residual polarization.

In this exemplary embodiment, first and second frequency values can be measured with respect to a water proton resonance frequency. The exemplary embodiment can also change $f_0$ to a new value within $-f_d$ and $f_d$, repeat the irradiating and simultaneous irradiating with frequencies based on changed $f_0$, and plot the residual polarization against $f_0$. The exemplary embodiment can also construct a $B_0$ map, identify two local minima on the plot corresponding to direct saturation of water protons; and can average two frequencies respectively at the two local minima. The exemplary embodiment can also quantify a precision estimate for a real water proton resonance frequency as $f_d$ minus the average of the two frequencies respectively at the two local minima. The exemplary embodiment can also correct a CEST contrast, including shifting the plot by the average of the two frequencies respectively at the two local minima to center on zero. The two frequency irradiation method can be performed without requiring an additional scan for a $B_0$ map.

In another exemplary embodiment are systems, methods and computer-readable mediums for isolating chemical exchange saturation including determining first and second frequencies, receiving a first data based on a first residual polarization of irradiation of a sample with both the first and second frequencies, determining third and fourth frequencies, receiving a second data based on a second residual polarization of irradiation of the sample with both the third and fourth frequencies, and determining a third data related to a chemical exchange saturation transfer contrast based on the first data and the second data.

In certain exemplary embodiments a further frequency is determined, a further data based on a further polarization of a further irradiation of the sample is received, and the CEST contrast is refined by separating different exchange mechanisms. The determination of the third data can be performed by subtracting the first data from the second data, where the subtracting eliminates a contribution of at least a direct solvent or medium saturation due to a pair-wise symmetric configuration. The subtracting can eliminate an MT contribution. The MT effects can be uniform over a frequency range, and can be used as an image contrast mechanism. The image contrast mechanism can be robust against B0 and B1 inhomogeneities.

In another exemplary embodiment are systems, methods and computer-readable mediums for removing magnetization asymmetry and correcting magnetic field ($B_0$) inhomogeneity including receiving a first data based on a simultaneous irradiation of a sample with a third frequency equal to a difference $f_d$ between a first frequency and a second frequency and a fourth frequency equal to a half sum $f_0$ of the first frequency and the second frequency, and determining a second data based on a residual polarization of the first data. The $f_0$ can be modified to a new value $f_1$ within about $-f_d$ and $f_d$, a third data can be received based on at least one further simultaneous irradiation with frequencies based on $f_1$ and plotted against $f_0$.

These and other objects, features and advantages of the exemplary embodiment of the present disclosure will become apparent upon reading the following detailed description of the exemplary embodiments of the present disclosure, when taken in conjunction with the appended claims.

BRIEF DESCRIPTIONS OF THE DRAWINGS

Further objects, features and advantages of the present disclosure will become apparent from the following detailed description taken in conjunction with the accompanying Figures showing illustrative embodiments of the present disclosure, in which:

FIGS. 1(a)-(d) are exemplary graphs illustrating exemplary irradiation data, according to exemplary embodiments of the present disclosure;

FIGS. 2(a) and 2(b) are exemplary graphs illustrating additional exemplary data at different frequencies, according to exemplary embodiments of the present disclosure;

FIGS. 3(a) and 3(b) are exemplary plots illustrating additional exemplary data at different frequencies, according to exemplary embodiments of the present disclosure;

FIGS. 4(a) and 4(b) are exemplary graphs illustrating additional exemplary data at different frequencies, according to exemplary embodiments of the present disclosure;

Figure 1:
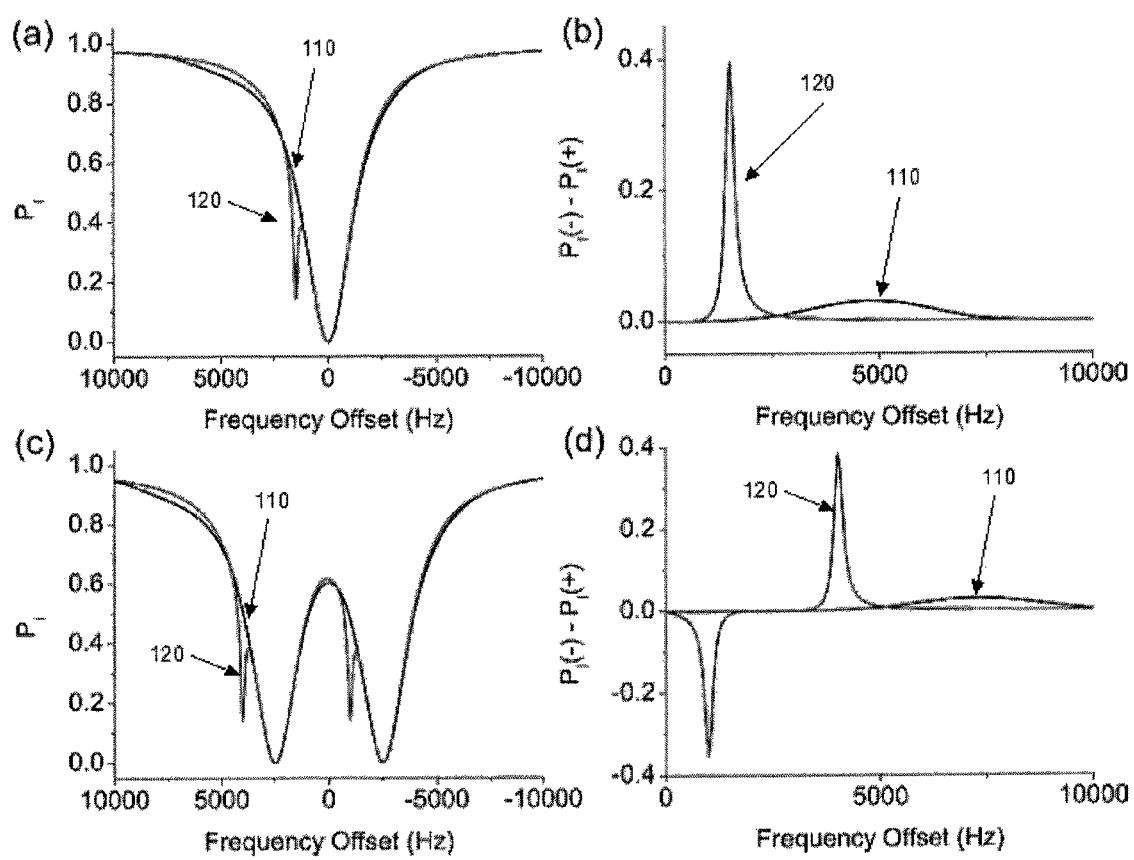

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures. It is intended that changes and modifications can be made to the described exemplary embodiments without departing from the true scope and spirit of the subject disclosure as defined by the appended claims.

DETAILED DESCRIPTION OF EXEMPLARY EMBODIMENTS

The exemplary systems, methods and computer-readable mediums of the present disclosure can establish a two-pool model for MT based on Provotorov's theory of saturation, and extend the model to describe the dynamics under simultaneous two-frequency irradiation. The exemplary embodiments of systems, methods and computer-readable mediums can isolate CEST from MT asymmetry effects, and can include a two-frequency CEST scheme for the quantification of CEST contrast. Various exemplary embodiments can be illustrated with an exemplary medium or solvent (e.g., water) but other mediums can also be possible. For example, the solvent or medium can consist of any molecule with rapidly exchangeable nuclei (e.g., water), alcohol (e.g., methanol, ethanol, etc.), small molecules with amide, sulfate, imino-groups, or other molecules that can accept an exchangeable moiety in a complex or adduct. Exemplary nuclei (e.g., protons), such as carbon, nitrogen, oxygen, fluorine, sodium, and/or phosphorous can be included.

The exemplary systems, methods and computer-readable mediums can establish a two-pool model with two-frequency RF irradiation. Previously, Provotorov's thermodynamic theory has been used to describe the dynamics of a strongly coupled spin system under weak RF irradiation. For example, the weak RF irradiation can be treated as a perturbation, which can solve the master equation by iteration to the second order under the assumption that the density operator can be described at all times by a quasi-equilibrium form which can be represented as $\rho(t)=(1/2^N)[1+\beta_S(t)\omega_0 S_z-\beta_d(t)H_d]$, where $\beta_S$ and $\beta_d$ can respectively be the Zeeman and dipolar inverse spin temperatures, $\omega_0$ can be the resonance frequency, and $H_d$ can be the dipole-dipole interaction Hamiltonian. By introducing the spin and dipolar polarizations $P_S=(2/N)\langle S_z\rangle$ and $P_d=(2N)(\langle H_d\rangle/\omega_{loc})$, the exemplary embodiments of systems, methods and computer-readable mediums can obtain an exemplary set of exemplary first-order coupled differential equations which can be represented as follows:

$$\frac{dP_S}{dt} = -W_S\left(P_S - \frac{\Delta}{\omega_{loc}}P_d\right) - \frac{P_S - P_{S,0}}{T_{1,S}} \quad (1)$$

and $$\frac{dP_d}{dt} = W_S\frac{\Delta}{\omega_{loc}}\left(P_S - \frac{\Delta}{\omega_{loc}}P_d\right) - \frac{P_d}{T_{1,d}} \quad (2)$$

where $\langle O\rangle \equiv tr\{O\rho\}$, $\omega_{loc}\equiv tr\{H_d^2\}/tr\{S_z^2\}$, $\Delta\equiv\omega_0-\omega$ can be the frequency difference between the resonance frequency $\omega_0$ and the frequency $\omega$ of the weak RF irradiation, $W_S=\pi\omega_1^2 g_S(\Delta)$, $\omega_1$ can be the amplitude of the weak RF irradiation, $g_S(\Delta)$ can be the normalized absorption line shape for a spin S, $T_{1,S}$ and $T_{1,d}$ can be the spin-lattice relaxation times for the Zeeman and dipolar reservoirs, respectively, and $P_{S,0}$ can be the thermal equilibrium polarization. Eq. 1 and Eq. 2 can be valid in both the rotating and laboratory frames.

To build a two-pool model for MT, the exemplary systems, methods and computer-readable mediums can add an additional Zeeman polarization $P_I$ without any dipolar reservoirs attached, representing protons in bulk water, for example. Following the same procedure leading to Eq. (1), it can be shown that the spin polarization can follow an exemplary kinetic equation which can be represented as:

$$\frac{dP_I}{dt} = -W_I P_I - \frac{P_I - P_{I,0}}{T_{1,I}} \quad (3)$$

Eq. (3) can be written in the laboratory frame and can be valid if $\omega_1 \ll \omega_0$. Thus, the changes in $P_I$ and $\Delta$ can be small on a time scale of the spin-spin relaxation time $T_2$ or the inverse of the line width. In addition, Eq. (3) can be derived without any assumptions about the form of $g(\Delta)$, and can give exactly the same steady state as the Bloch equations with a Lorentzian line shape $g_{Lorentz}(\Delta)=(T_2/\pi)[1+(\Delta T_2)^2]^{-1}$.

A two-pool model for MT can be established by combining Eqs. (1), (2), and (3) and adding exchange terms. It can be assumed that the exchange between the two pools is a first-order process. The exemplary equations represented as:

$$\frac{dP_I}{dt} = -W_I P_I - \frac{P_I - P_{I,0}}{T_{1,I}} + k_{S\to I}P_S - k_{I\to S}P_I, \quad (4)$$

$$\frac{dP_S}{dt} = -W_S\left(P_S - \frac{\Delta}{\omega_{loc}}P_d\right) - \frac{P_S - P_{S,0}}{T_{1,S}} + k_{I\to S}P_I - k_{S\to I}P_S, \quad (5)$$

and $$\frac{dP_d}{dt} = W_S\frac{\Delta}{\omega_{loc}}\left(P_S - \frac{\Delta}{\omega_{loc}}P_d\right) - \frac{P_d}{T_{1,d}} \quad (6)$$

and can be used to describe MT phenomena. By setting $P_d=0$, the relevant expressions can be obtained for the description of CEST phenomena. $\Delta$ can be measured from the resonance of spin I and the chemical shift of spin S can be imbedded in the line shape function $g_S(\Delta)$.

With additional irradiation frequencies, it may not be possible to use a rotating frame in which the description of the dynamics can become more complicated due to the time-dependent Hamiltonian. On the other hand, the accommodation of additional weak RF irradiation can be straightforward (e.g., in the laboratory frame). If the differences between irradiation frequencies is much larger than the amplitudes of the RF fields, the cross effect caused by the simultaneous existence of two RF fields can be shown to be negligible, and each frequency can contribute to the kinetics (e.g., in the same way as in Eqs. (1), (2) or (3)). Therefore, the exemplary kinetic equations for a two-pool model for MT, with a dipolar reservoir and under two-frequency RF irradiation, can be represented by:

$$\frac{dP_I}{dt} = -W_I P_I - W_I' P_I - \frac{P_I - P_{I,0}}{T_{1,I}} + k_{S\to I}P_S - k_{I\to S}P_I, \quad (7)$$

$$\frac{dP_S}{dt} = -W_S\left(P_S - \frac{\Delta}{\omega_{loc}}P_d\right) - \quad (8)$$

$$W_S'\left(P_S - \frac{\Delta'}{\omega_{loc}}P_d\right) - \frac{P_S - P_{S,0}}{T_{1,S}} + k_{I\to S}P_I - k_{S\to I}P_S,$$

and $$\frac{dP_d}{dt} = W_S\frac{\Delta}{\omega_{loc}}\left(P_S - \frac{\Delta}{\omega_{loc}}P_d\right) + W_S'\frac{\Delta'}{\omega_{loc}}\left(P_S - \frac{\Delta'}{\omega_{loc}}P_d\right) - \frac{P_d}{T_{1,d}}, \quad (9)$$

where the primed symbols W' and Δ' can be the transition rate and the offset for the second RF irradiation at ω'. Similarly, CEST under two-frequency RF irradiation can be described by Eqs. (7) and (8) with $P_d=0$.

By setting $dP_I/dt=dP_S/dt=dP_d/dt=0$, Eqs. (7), (8), and (9) can give the steady-state solutions $P_{I,\infty}$, $P_{S,\infty}$ and $P_{d,\infty}$, and can be represented as:

$$P_{I,\infty} = \frac{(P_{I,0}/T_{1,I})[(W_I + W_I' + 1/T_{1,I} + k_{I\to S}) - B] +}{A - (W_I + W_I' + 1/T_{1,I} + k_{I\to S})B} \quad (10)$$

$$P_{S,\infty} = \frac{(P_{I,0}/T_{1,I})k_{I\to S} + (P_{S,0}/T_{1,S})(W_I + W_I' + 1/T_{1,I} + k_{I\to S})}{A - (W_I + W_I' + 1/T_{1,I} + k_{I\to S})B}, \quad (11)$$

and $$P_{d,\infty} = P_{S,\infty} \frac{B\omega_{loc}}{W_S\Delta + W_S'\Delta'}, \quad (12)$$

where $A \equiv (W_I+W_I'+1/T_{1,I}+k_{I\to S})(W_S+W_S'+1/T_{1,S}+k_{S\to I})-k_{I\to S}k_{S\to I}$ and $B \equiv (W_S\Delta+W_S'\Delta')^2/(W_S\Delta^2+W_S'\Delta'^2+\omega_{loc}^2/T_{1,d})$.

The exemplary systems, methods and computer-readable mediums can solve Eqs. (4), (5), and (6) numerically to check whether they produce a proper two-pool model. Different examples can be investigated depending on the spectral parameters given to spin S (e.g., the MT and CEST cases).

According to the exemplary systems, methods and computer-readable mediums, the relaxation times for spin I (e.g., $T_{1,I}$=5 s and $T_{2,I}$=1 s), can be set to be similar to those of a water proton NMR signal in chondroitin sulfate ("CS") solution. The same $T_1$ relaxation time can be used for spin S (e.g., $T_{1,S} \equiv T_{1,I}$), because the concentration of spin S can be set to be small. Further, the initial and equilibrium polarizations $P_{I,0}$ and $P_{S,0}$ can be assumed to be 0.99 and 0.01. Therefore, it can be assumed that the major relaxation mechanism for spin S can be due to the fluctuating dipolar field from spin I, which can make the $T_1$ relaxation times similar. The resonance frequency of spin S can be set to be 1500 Hz, which can be the frequency offset measured from the resonance frequency of spin I. This value can be close to the chemical shift (e.g., 3.2 parts per million ("ppm")) of amide protons relative to the water signal in cartilage at 11.74 T.

The line shape of spin I can be assumed to be Lorentzian. For the CEST case, the line shape of spin S can also be set to Lorentzian with $T_{2,S}$=1 s. The exchange rates $k_{I\to S}$ and $k_{S\to I}$ can be set to 1 s$^{-1}$ and 99 s$^{-1}$, respectively, and can be 3 to 5 times higher than the reported chemical exchange rates of amid protons. For the MT case, it can be assumed that spin S can have a Gaussian line shape with $\omega_{loc}=2\pi\times$ 1000 Hz or $g_S(\Delta)=\exp[-(\Delta-2\pi\times1500 \text{ Hz})^2/(6\omega_{loc}^2)]/\sqrt{6\pi}\omega_{loc}$). The exchange rates $k_{I\to S}$ and $k_{S\to I}$ can be set to 0.01 s$^{-1}$ and 0.99 s$^{-1}$, respectively, to produce the Z spectra similar with those of the CEST case, and can be about 10% of the proton exchange rates of gelatin.

As shown in FIG. 1(a), the numerically calculated $P_I$ after a 5 s-long RF irradiation with $\omega_1/2\pi$=100 Hz can be plotted against the frequency offsets of the RF irradiation, which can be the so-called Z spectra. FIG. 1(b) shows an exemplary plot of the asymmetries of the Z spectra, which can be obtained by subtracting $P_I$'s at the positive frequency offsets from $P_I$'s at the corresponding negative frequency offsets (e.g., $P_I(-\Delta)-P_I(+\Delta)$). The MT case can be illustrated in FIGS. 1(a)-(d) as the line 110, while the CEST case can be illustrated with line 120.

As shown in FIG. 1(c), the Z spectra of spin I after a 5 s-long two-frequency RF irradiation with the RF amplitudes $\omega_1=\omega_1'=2\pi\times100$ Hz and the distance between the two frequency components $|\Delta-\Delta'|=2\pi\times5000$ Hz can be plotted against the central frequency offsets $(\Delta-\Delta')/2$. For example, the zero frequency offset in the Z spectra can mean that the saturating RF irradiation can be applied at frequency offsets of ±2500 Hz. Similarly, the asymmetries of the Z spectra can be calculated as $$P_I\left(-\frac{\Delta+\Delta'}{2}\right) - P_I\left(+\frac{\Delta+\Delta'}{2}\right)$$

as shown in FIG. 1(d).

With two-frequency RF irradiation, the duplication of the Z spectrum can be expected as each frequency component can independently sweep the resonance of spin I, which is shown in FIG. 1(c). If the distance between the two frequency components is larger than the chemical shift difference between spins I and S, the peaks due to direct saturation and CEST effect can appear as a duplicated Z spectrum pattern, separated by the frequency spacing of the irradiation, as seen in FIG. 1(c). If the two frequency separation between the two RF components is smaller than the chemical shift difference, the patterns will overlap with the two CEST dips appearing on one side of the water dips. As a result, the asymmetry curve will have only negative peaks.

The asymmetry curves of the Z spectra obtained with two-frequency RF irradiation can be shown in FIG. 1(d). While the CEST case can reveal two peaks in the asymmetry curve, the MT case can produce a flat region when the frequency offset is small, followed by a positive peak at the larger frequency offset, which can look similar to the peak in the asymmetry curve shown in FIG. 1(b). The flat region can be explained by the uniform saturation of spin S when both frequency components lie within the spectrum of spin S, resulting in the uniformity of the MT effect. The positive peak can appear when the frequency offset is large enough such that only one frequency component touches the spectrum of spin S, and MT is no longer uniform.

The Z spectra under single- and two-frequency RF irradiations can be obtained from CS solution, gelatin, and a bovine cartilage piece. These samples can respectively represent the CEST, MT, and mixed (e.g., CEST+MT) cases. All NMR experiments can be performed using a NMR spectrometer (e.g., a Bruker Avance 500 MHz NMR spectrometer). To reduce radiation damping effects, the probe can be detuned to approximately 508 MHz. Depending on the exact tuning and matching conditions, the duration of the 360° pulse can be between 230 μs and 264 μs.

The exemplary CS solution can be prepared by dissolving a CS sodium salt from bovine cartilage in a 50:50 $H_2O/D_2O$ solution which can result in a particular concentration (e.g., a concentration of 1% wt). The spin-lattice and spin-spin relaxation times for the water protons peak can be 5.8 sec and 880 ms, respectively. The Z spectra can be obtained with a 2 sec-long RF irradiation followed by a 5° reading pulse. The amplitude of the 2 sec-long RF irradiation ($\gamma B_1/2\pi$) can be 100 Hz, and each run can be repeated twice while alternating the phase of the RF irradiation in order to kill residual transverse magnetization. The recycle delay can be set to 40 seconds. Two-frequency RF irradiation can be implemented by cosine pulses with the modulation frequencies being about 1 kHz to 4 kHz, or any frequency therebetween, although not limited thereto. The amplitude of the cosine pulses can be set to 200 Hz, so each frequency component can have the amplitude of about 100 Hz. The frequency of the single-frequency RF irradiation, or the center frequency of the cosine pulses, can be stepped from −4500 Hz to 4500 Hz at intervals of 100 Hz, although not limited thereto.

Figure 2:
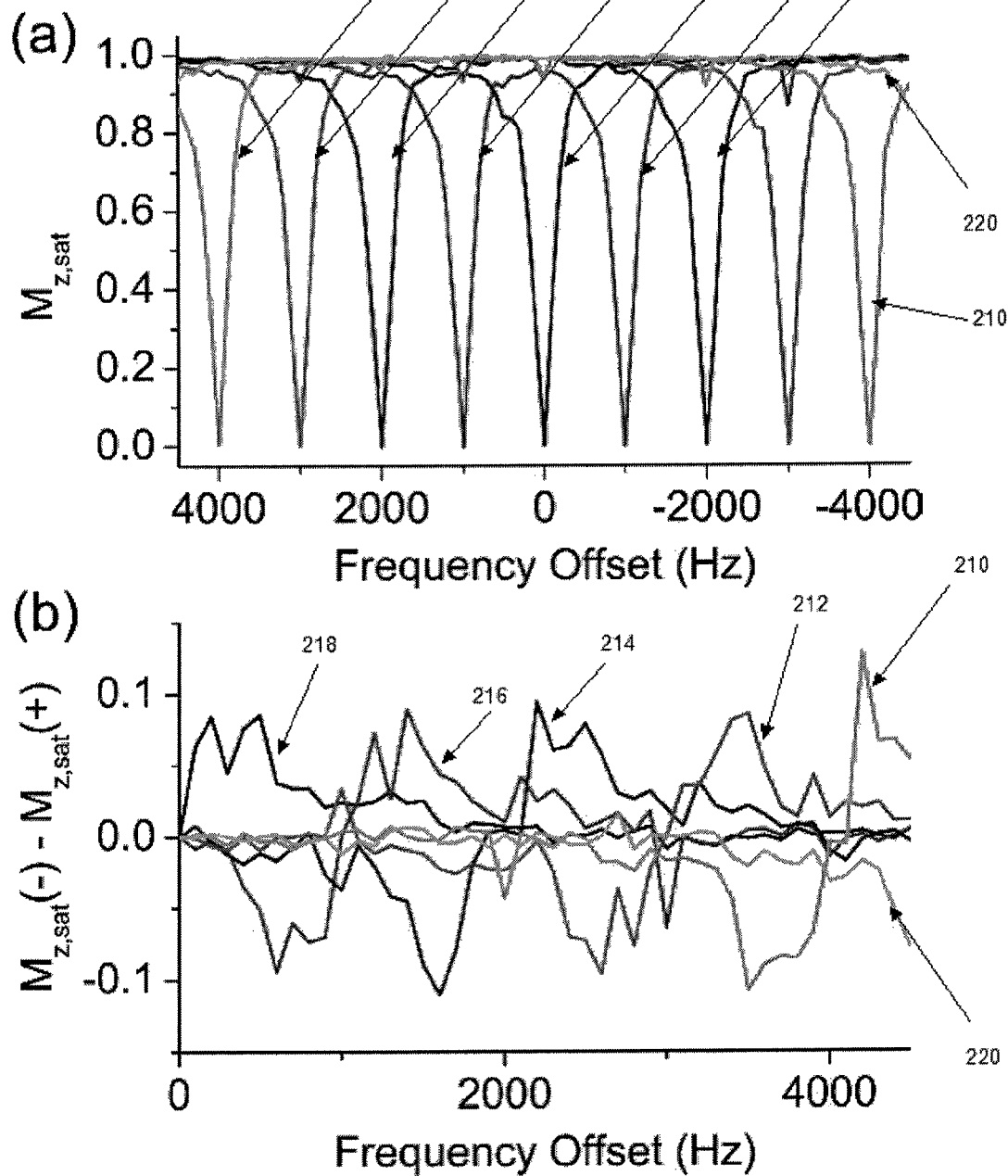

The Z spectra measured from the CS solution and their asymmetry curves are shown in FIG. 2. There are two groups of exchangeable protons (—NH and —OH) in the CS molecule, and two non-exchangeable MT sites (CH and N-acetyl residues), which give a broad positive bump spanned from 0 Hz to 1500 Hz in the asymmetry curve obtained with single-frequency RF irradiation (e.g., line 218 in FIG. 2(B)). Using exemplary two-frequency RF irradiation, those CEST sites can be scanned (e.g., two times during the measurement of the Z spectra as illustrated in FIG. 2(A)) and can appear as one negative and one positive peak in the asymmetry curves (e.g., as illustrated in FIG. 2(B)), which is consistent with the CEST case discussed above with respect to the equations. Further, in FIGS. 2(A) and 2(B), the line 218 can illustrate the single-frequency RF irradiation, while lines 216, 214, 212, and 210 can illustrate cosine pulses with the modulation frequencies 1 kHz, 2 kHz, 3 kHz, and 4 kHz, respectively.

For the exemplary gelatin sample, gelatin powder (e.g., type B from bovine skin) can be dissolved in heated water, then cooled down to the room temperature in order to obtain the gelatinous state. The concentration of gelatin can be any ratio (e.g., 15% wt), and the gel can be put into, e.g., a 3 mm o.d. NMR tube. The tube can be placed in, e.g., a 5 mm o.d. NMR tube filled with $D_2O$. This separation from $D_2O$ can be done because the RF power, through the deuterium lock channel, can interfere with the proton NMR when gelatin is prepared in a mixture of $H_2O$ and $D_2O$. The spin-lattice and spin-spin relaxation times of the water proton peak can be 2 sec and 100 ms, respectively, although not limited thereto. The relaxation delay can be set to 20 seconds, although not limited thereto. The single-frequency and two-frequency RF irradiations can be applied for 0.5 seconds and followed by a 5° reading pulse. For two-frequency RF irradiations, cosine pulses with modulation frequencies from 1 kHz to 6 kHz could be used, or any other frequency, including frequencies therebetween can be used. The frequency of the single-frequency RF irradiation and the center frequencies of the cosine pulses can be varied from −8000 Hz to +8000 Hz at intervals of 100 Hz, although not limited thereto.

Figure 3:
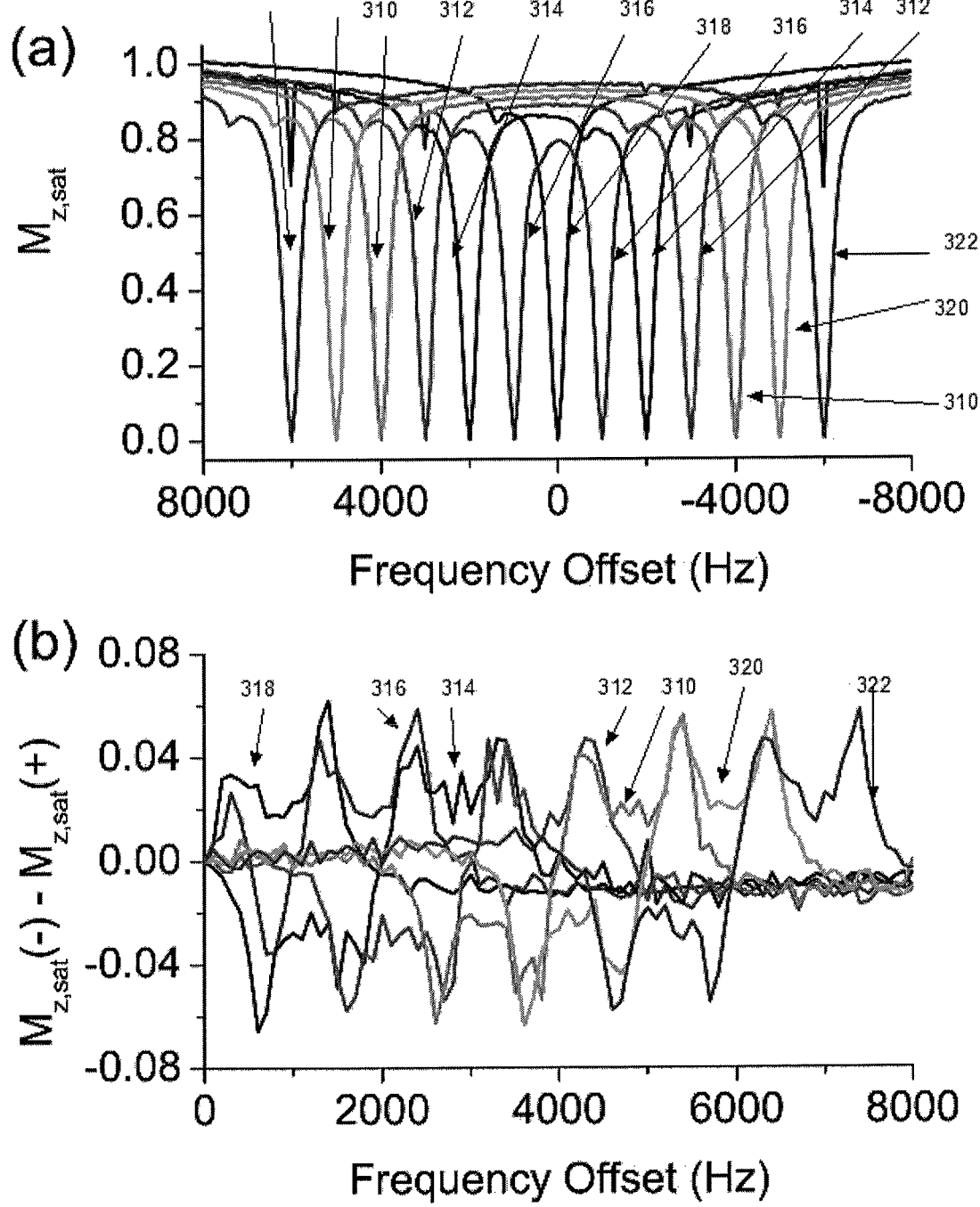

FIGS. 3(a) and 3(b) illustrate Z spectra and associated asymmetry curves of water protons in Gelatin. Line 318 was measured with the single-frequency RF irradiation, and the lines 316, 314, 312, 310, 320, and 322 were measured with cosine pulses with the modulation frequencies 1 kHz, 2 kHz, 3 kHz, 4 kHz, 5 kHz, and 6 kHz, respectively. The Z spectrum of gelatin, obtained with single-frequency RF irradiation, can reveal a narrow spike at 1400 Hz or 2.8 ppm downfield from the water protons resonance (line 318 in FIG. 3(a)), which could indicate that gelatin can contain some exchangeable protons. When the asymmetry curve is plotted (line 318 in FIG. 3(b)), there can exist two narrow positive peaks between 0 Hz and 2000 Hz, and the asymmetry can stay negative beyond 2000 Hz, which can indicate that this MT pool should have its center frequency on the upfield side of the water protons resonance. The Z spectra obtained with cosine pulses or two-frequency RF irradiation can show two dips due to direct saturation of water protons together with the narrow spike duplicated. Compared with the Z spectra from the CS solution, the Z spectra from gelatin can show less signal intensity of water protons between two direct-saturation dips, which can be an indication of MT between water protons and protons in gelatin. The intensity can depend on the modulation frequency of the cosine pulses (e.g., the larger the modulation frequency, the less saturation was observed).

FIG. 3(b) shows exemplary asymmetry curves. The narrow spike at 1400 Hz can produce two peaks, one negative and one positive, in the asymmetry curves. The asymmetry curve from single-frequency RF irradiation can stay negative when the frequency offset is large (e.g., greater than 2000 Hz), which can suggest that the MT effect is not symmetric around the water resonance. For some cosine pulses, for example, when the modulation frequency was 3 or 4 kHz, the asymmetry was zero around the zero frequency until the negative peak appeared, as with the MT case discussed above with respect to the equations. By contrast, when the cosine pulses with larger modulation frequencies were applied (e.g., 5 or 6 kHz), the asymmetry curves can deviate from zero and can move to the positive direction before the negative peak appeared. This deviation can be exactly the opposite of the broad negativeness observed in the asymmetry curve from single-frequency RF irradiation, which can suggest that the situation is more like the CEST case, and that the distance between two frequency components can be larger than the spectral range of the protons causing this MT effect.

In another exemplary set-up, a bovine articular cartilage piece can be cut from a frozen patella (e.g., without a bone segment), and placed in phosphate buffered saline solution for about an hour. The cartilage piece can then be blotted dry and put into a 3 mm o.d. NMR tube with Fluorinated oil (e.g., Fluorinert, FC-84, Oakwood), which can fill the void spaces for protection and reduction of susceptibility artifacts. Similar to the exemplary gelatin sample, the 3 mm o.d. NMR tube can be placed in a 5 mm o.d. tube filled with $D_2O$ for the deuterium lock. The spin-lattice and spin-spin relaxation times for water protons were measured to be 4.2 sec and 80 ms, respectively. For the Z spectra, the same pulse sequence parameters can be used as with the exemplary CS solution, except that one more Z spectrum can be measured with a cosine pulse with the modulation frequency of 5 kHz.

The Z spectrum obtained with single-frequency RF irradiation (line 418 in FIG. 4(A)) can illustrate a single dip around the zero frequency offset, and much less intensity of water protons for all the frequency offsets compared with the CS and gelatin samples, which can be evidence for prevailing MT effects. Cartilage could have some exchangeable protons, which can be barely seen in the Z spectrum. However, the corresponding asymmetry curve (line 418 in FIG. 4(b)) shows one narrow peak around 500 Hz or 1 ppm, which can be assigned to CEST between water and —OH protons. At larger frequency offsets, the curve can convert into a broad negative baseline offset, which can be interpreted as large MT asymmetry effects.

The Z spectra obtained with cosine pulses, as shown in FIG. 4(a), can illustrate that the signal intensities of water protons can become significantly smaller even when any of the two frequency components do not directly saturate the water protons. Similar to the exemplary case of gelatin, the signal intensity of water protons can depend on the modulation frequency used in a cosine pulse. The corresponding asymmetry curves, as shown in FIG. 4(b), can illustrate that the asymmetry can remain zero when the frequency offsets were small, and until the negative peak appeared. Note that the integral of the asymmetry peak due to CEST can become smaller with two-frequency RF irradiations as compared with single-frequency RF irradiation. When normalized to the integral of the asymmetry peak with single-frequency RF irradiation, the integrals of the negative asymmetry peaks can be 0.55, 0.77, 0.92, and 0.87 for the cosine pulses with the modulation frequencies of 1 kHz, 2 kHz, 3 kHz, and 4 kHz, respectively, which are illustrated as lines 416, 414, 412, 410, 420 respectively, although not limited thereto. The negative peaks can be chosen for this comparison because they can appear at smaller frequency offsets where MT contributions are supposed to be minimal, as seen from the numerical equations discussed above. If the areas of the negative asymmetry peaks from the cosine pulses with the modulation frequencies of 2 kHz, 3 kHz, and 4 kHz are taken into consideration, the average area can be 0.85, and the standard deviation can be 0.06. The area from the cosine pulse with the modulation frequency of 1 kHz is not included because it can be significantly smaller, which could be caused by the simultaneous saturation of different CEST and NOE sites in the exemplary cartilage.

The validity of Eq. (3) can be based on the assumption that a given system can be at all times in a state close to internal equilibrium, and that the state does not change much over time. While Eqs. (1) and (2) are known to be valid if $\omega_1 \ll \omega_{loc}$, there is no such condition for Eq. (3). Therefore, Eq. (3) could be applicable even if the amplitude of the applied RF field $\omega_1$ were larger than the spectral linewidth. For example, Eq. (3) can predict the same steady-state solutions, regardless of the value of $\omega_1$, as Bloch equations (e.g., where the lineshape is Lorentizan). On the other hand, the applied magnetic field can cause the Larmor precession of the magnetization vector, which can mean large and fast changes in the spin state. Eq. (3) may not be applied unless such Larmor precession is suppressed fast enough, which can happen, for example, when a given system has fast transverse relaxation.

The exemplary systems, methods and computer-readable mediums can use Provotorov's theory of saturation to establish a system of kinetic equations for MT and CEST phenomena, and can clarify how line shape functions other than Lorentzian can be accommodated in the exemplary results. This is a surprising result from the perspective of starting from the formalism based on the Bloch equations. In addition, two or more simultaneous RF irradiations can be dealt easily with the exemplary systems, methods and computer-readable mediums. The uniformity of the MT effect can occur as long as the two frequency components simultaneously touch the spectrum of spin S. From the exemplary gelatin arrangement, for example, the positive asymmetry peak can be produced when the modulation frequency can be 5 or 6 kHz (lines 320 and 322 of FIG. 3(B)). In practice, it can be useful to determine the optimal distance between the two frequency components for a given sample such that the uniformity of the MT effect can be achieved.

Cosine modulated pulses can be used to apply two RF frequencies symmetrically around their center frequencies. They can be implemented as digitized shapes with 50,000 steps for 0.5 sec-long pulses and 100,000 steps for 2 sec-long pulses, although not limited thereto. The number of steps should be large enough to approximate a continuous time variation of the RF amplitudes even at the highest modulation frequency for the given pulse duration. However, the experimental results showed spikes in the Z spectra at multiples of the modulation frequencies of the cosine pulses. For example, big spikes can be observed specifically at triple the modulation frequencies, which likely arose from digitization and truncation errors.

The exemplary systems, methods and computer-readable mediums can include a two-frequency CEST simulation. Specifically, the exemplary numerical simulations and illustrative experiments presented herein can suggest that it is possible to separate CEST effects from MT effects with two-frequency saturation. For example, the exemplary systems, methods and computer-readable mediums can make the MT effect uniform with two-frequency irradiation such that only CEST effects contribute to the asymmetry of the Z spectra. Then, the effect of direct saturation of water can be addressed by irradiating a given system at the opposite side of the water spectrum and subtracting the results. Therefore, so-called two-frequency CEST contrast can be estimated by combining two two-frequency irradiations. Their irradiation frequencies can be pair-wise symmetric with respect to the resonance frequency of water protons, and one of the four frequency positions can be located on the resonance frequency of an exchangeable proton. Additionally, more efficient uniform saturation of MT effects can be performed by choosing the two frequency positions on opposite sides around the center frequency of the protons responsible for the MT effect. These positions, however, may not in general be known directly because the spectra can often be overlapped by the strong water signal. However, the exemplary systems, methods and computer-readable mediums can estimate the positions through Z spectra.

Exemplary Uniform MT Contrast

The MT effects can be made uniform, and can be used as an image contrast. For $f_1$ and $f_2$ (the two irradiation frequencies), and $f_0$ for the center frequency, such contrast can be defined as $1-M_{z,sat}(f_1, f_2)$, where $M_{z,sat}$ can be the solvent or water signal after simultaneous irradiation at the indicated frequencies. These frequencies can be chosen over a wide range, and thus can be chosen to avoid any direct water saturation or CEST effects. When $f_d$ is larger than 5 or 6 ppm, $M_{z,sat}(-0.5\ f_d, 0.5\ f_d)$, the signal can be determined purely by MT effects as the direct water saturation and CEST effects may not be induced. This uniform-MT contrast can be robust against $B_0$ and $B_1$ inhomogeneities, since the precise choice of irradiation frequencies may not important.

Figure 10:
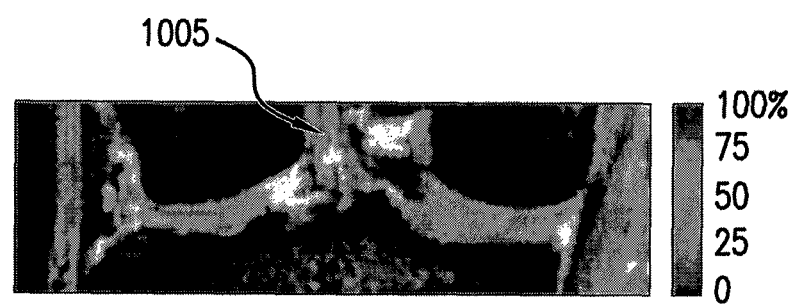
FIG. 10 is an exemplary picture of a uniform magnetization transfer contrast in the articular cartilage according to exemplary embodiments of the present disclosure.

The uniformity of the MT effect can be checked by the flatness of the Z spectrum around $f_0=0$ Hz. If $f_d$ is larger than the range of a spectrum of protons causing MT effects, the condition of the simultaneous saturation may not be met, and the Z spectrum can be inclined around $f_0=0$ Hz. For example, as shown in FIG. 10, cartilage tissue and synovial fluid in a knee joint 1005 can be separated by plotting a uniform-MT ("uMT") contrast. The regions with more MT effects or higher uMT contrast can belong to cartilage tissue, and those with less MT effects of lower uniform-MT contrast can belong to synovial fluid.

Figure 11A:
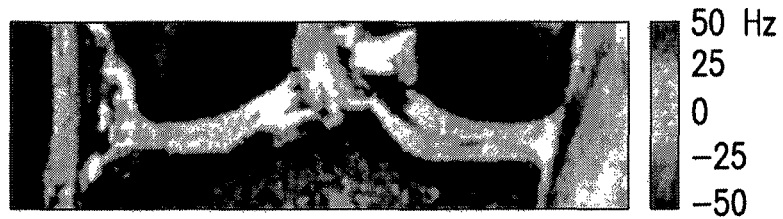
FIG. 11(a) is an exemplary illustration of an articular cartilage according to a prior art contrast method.
Figure 11B:
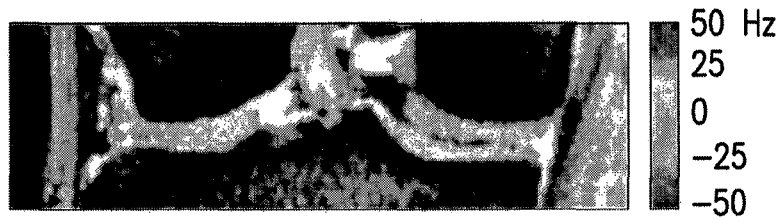
FIG. 11(b) is an exemplary illustration of the articular cartilage according to an exemplary uniform Magnetization Transfer according to exemplary embodiments of the present disclosure.

FIGS. 11(a) and 11(b) show exemplary pictures showing CEST contast due to glycosaminoglycans (GAGs), also called gagCEST. To obtain this specific contrast, integration is performed over the frequency offsets from 0 Hz to 600 Hz in the articular cartilage of a healthy volunteer from a prior art contrast method (FIG. 11(a)) and the exemplary uniform Magnetization Transfer (FIG. 11(b)).

Figure 12A:
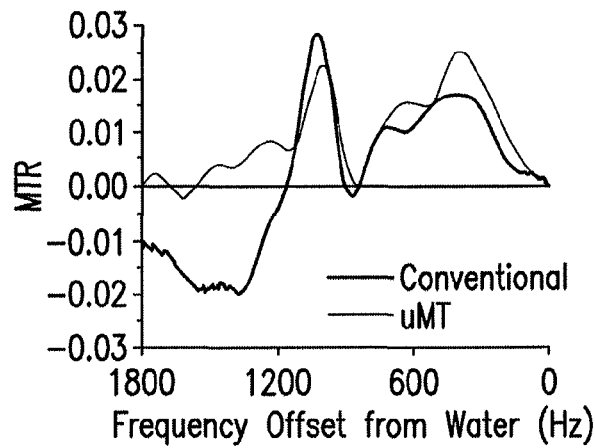
FIG. 12(a) is an exemplary graph showing an asymmetry curve of lateral cartilage according to an exemplary embodiment of the present disclosure.
Figure 12B:
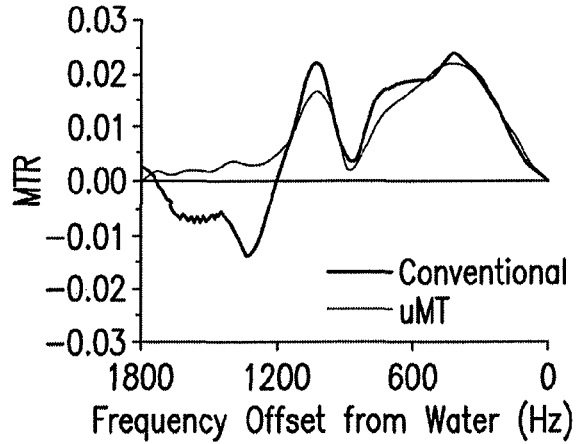
FIG. 12(b) is an exemplary graph showing an asymmetry curve of medial cartilage according to an exemplary embodiment of the present disclosure.

FIGS. 12(a) and 12(b) show exemplary MT asymmetry curves in pixels with larger MT effects on the lateral (FIG. 12(a)) and medial (FIG. 12(b)) femorotibial cartilage obtained from images (e.g., FIG. 11(b)) with different irradiation frequencies showing that MT asymmetry can be suppressed over a large range using the two-frequency irradiation sequence.

The exemplary systems, methods and computer-readable mediums can define the two-frequency CEST in a compact form as $CEST_{two\ freq}(\Delta_1, \Delta_2)=M_{z,sat}(\Delta_1, \Delta_2)-M_{z,sat}(-\Delta_1, -\Delta_2)$, where $\Delta_{1,2}$ can be the frequency positions measured from the resonance frequency of water protons and can be such that both frequencies simultaneously touch the spectrum of the protons which contribute to the MT effects, and $\Delta_1$ can be the chemical shift of an exchangeable proton measured from the resonance frequency of water protons. To avoid any interference due to the proximity of the two frequency positions and the possibility of simultaneous touch on multiple CEST sites, $\Delta_2$ can be chosen to be more than a particular number (e.g., 5 or 6 ppm) away from the water resonance, thus being outside of the typical range of proton chemical shifts.

The exemplary systems, methods and computer-readable mediums can include a two-pool model for MT and CEST based on Provotorov's theory of saturation. In the exemplary systems, methods and computer-readable mediums, the two frequency components can simultaneously touch the broad spectrum of protons in macromolecules such that the magnetization of those protons can be uniformly saturated over a broad spectrum, and the MT effect on the water protons can be made uniform. Then, the exemplary systems, methods and computer-readable mediums can remove the MT asymmetry, which can exist when single-frequency RF irradiation is applied. The spectrum of a CEST agent, conversely, can be typically very narrow such that two-frequency RF irradiation can merely duplicate the CEST effect. Based on this distinction between MT and CEST effects under two-frequency RF irradiation, the exemplary systems, methods and computer-readable mediums can define a two-frequency CEST scheme that can isolate CEST effects from the MT effects, and can be useful to quantify CEST contrast.

Figure 5:
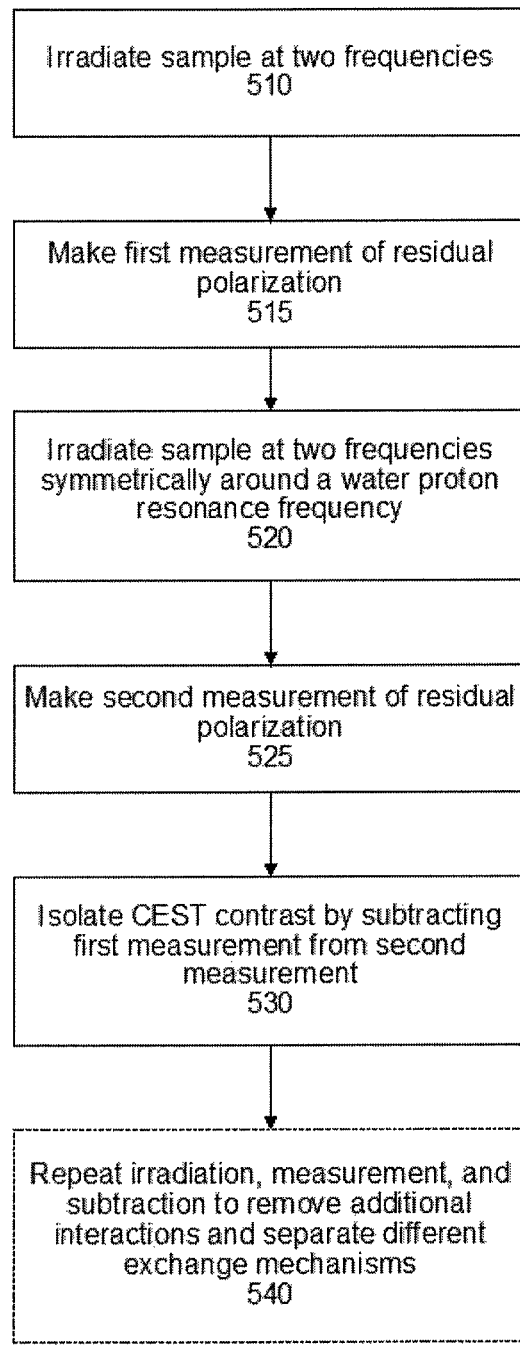
FIG. 5 is an exemplary flow diagram illustrating an exemplary method according to exemplary embodiments of the present disclosure.
Figure 6:
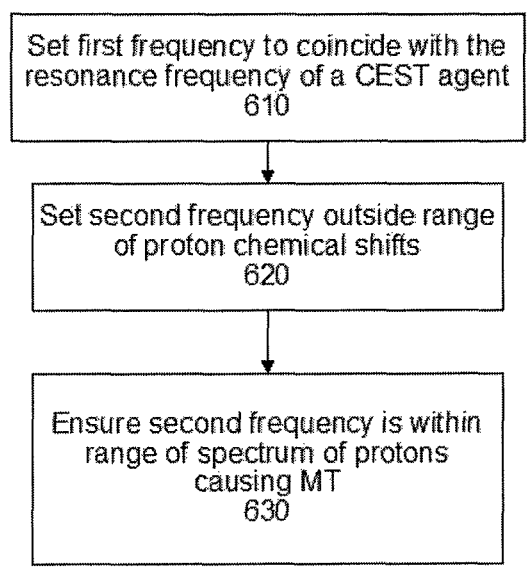
FIG. 6 is an exemplary flow diagram illustrating an exemplary method according to exemplary embodiments of the present disclosure.

FIG. 5 illustrates an exemplary flow diagram including an exemplary method for removing MT asymmetry. First, at block 510 a sample can be irradiated by RF at two distinct frequencies, and the measurement of residual polarization can be performed at procedure 515. FIG. 6 illustrates an exemplary expansion of exemplary procedures 510 and 515 from FIG. 5.

The exemplary systems, methods and computer-readable mediums, as part of the first irradiation at procedure 510, and first polarization measurement at procedure 515, can set the first frequency to coincide with the resonance frequency of a CEST agent at procedure 610 of FIG. 6. Next, at procedure 620 of FIG. 6, a second frequency can be chosen to be outside of the typical range of proton chemical shifts (e.g., more than 5 or 6 ppm away from the water proton resonance), and in order to avoid interference with the bulk water resonance, the CEST agent resonance or other possible CEST agents that can be present. Finally, at procedure 630 of FIG. 6, the exemplary method can ensure that the second frequency is within the range of the spectrum of protons causing magnetization transfer effects (e.g., such that those protons experience simultaneous saturation by two frequencies). MT can be caused by nuclei interacting or exchanging with immobile environments, thus exhibiting very broad spectra. As a result, the exemplary systems, methods and computer-readable mediums can have considerable freedom in the choice of the second frequency (e.g., within a range of 10-50 ppm).

Returning to FIG. 5, at procedure 520, a sample can be irradiated by RF at two distinct frequencies. The positions of the two frequencies in this irradiation can be located symmetrically to the first and second frequencies, respectively, with respect to the water proton resonance frequency, but far away from the two frequencies chosen above. The two frequencies can also be within the range of the spectrum of protons causing magnetization transfer effects such that those proton's experience simultaneous saturation by two frequencies.

At procedure 530, CEST contrast can be isolated by subtracting the result of the first measurement (e.g., from procedure 515) from the result of the second measurement (e.g., from procedure 525). The first measurement result can consist of contributions by CEST, MT, and direct water saturation. The second measurement result can consist of contributions by MT and direct water saturation. The contribution of direct water saturation can cancel out due to the pair-wise symmetric configuration. The contribution of MT can also cancel out because the simultaneous two-frequency RF irradiation can make the MT effects uniform and independent of the positions of two frequencies. Once the direct water saturation and MT are cancelled out, generally only the CEST contrast remains.

At procedure 540, the exemplary systems, methods and computer-readable mediums can perform additional steps at procedure 540 (e.g., repeating the irradiation, measurement, and subtractions to remove additional interactions and separate the different exchange mechanisms).

Figure 7:
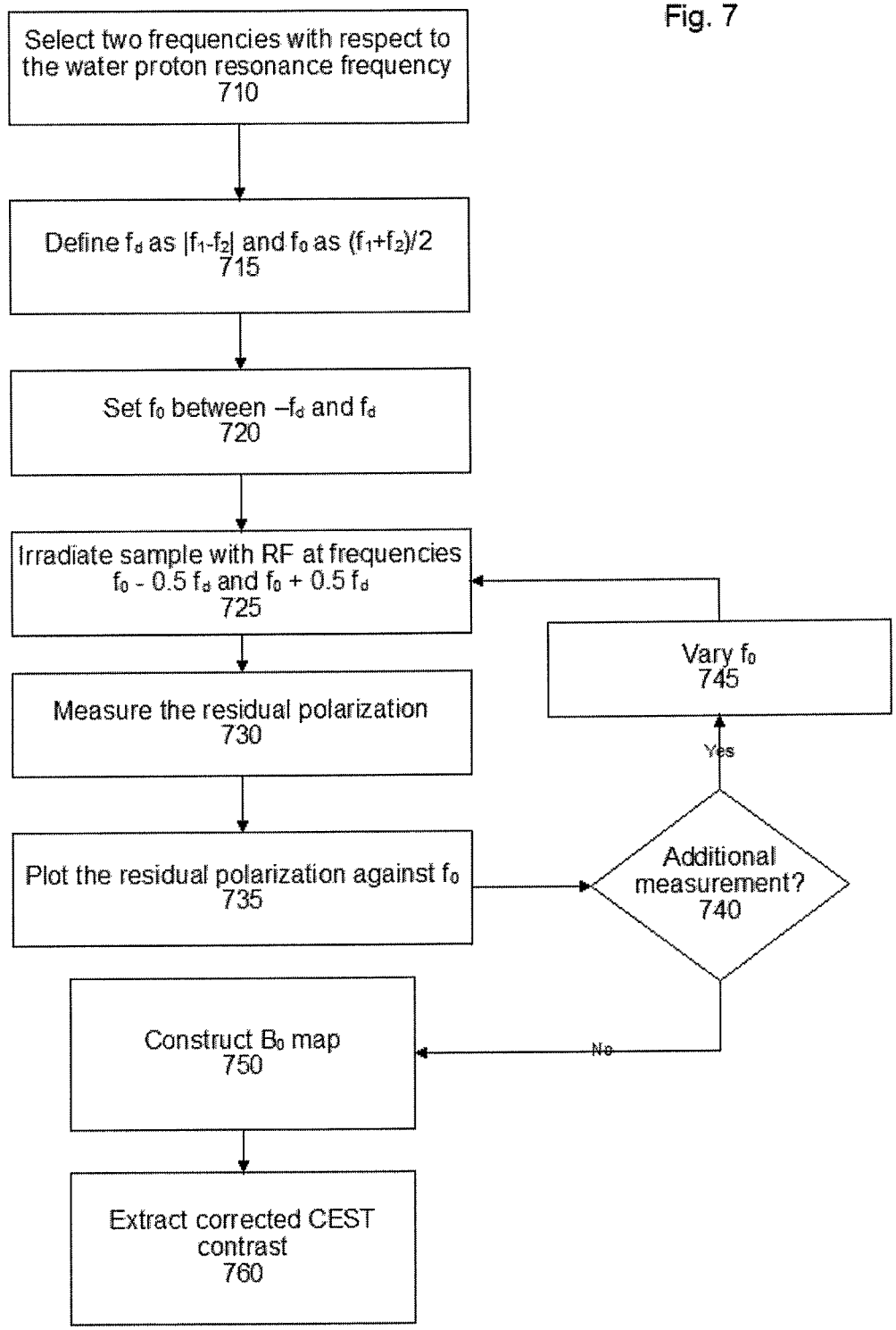
FIG. 7 is an exemplary flow diagram illustrating a further exemplary method according to exemplary embodiments of the present disclosure.

As shown in FIG. 7, the exemplary systems, methods and computer-readable mediums can include a static magnetic field ($B_0$) inhomogeneity correction. This can create a more accurate estimation of CEST contrast by a $B_0$ inhomogeneity correction. Since the same dataset can be used to construct a $B_0$ map and correct the $B_0$ inhomogeneity, the exemplary systems, methods and computer-readable mediums can be robust against any change of the local static magnetic field in time, which can be an issue when the $B_0$ inhomogeneity is independently measured (e.g., with a single frequency). To correct the $B_0$ inhomogeneity effect, data can be collected with at least two varying irradiation frequencies, while keeping the distance between two frequencies constant.

The exemplary method of FIG. 7 can collect the varying data starting at procedure 710, by selecting two frequencies, $f_1$ and $f_2$, whose values can be measured with respect to the water proton resonance frequency. At procedure 715, $f_d$ can be defined as $|f_1-f_2|$ and $f_0$ as $(f_1+f_2)/2$. Each measurement can be performed by first setting $f_0$ between $-f_d$ and $f_d$. Initially, this can be done at procedure 720. For repeated measurements, this can be done at procedure 745. Next, at procedure 725, a sample can be irradiated with RF at two frequencies, $f_0-0.5\ f_d$ and $f_0+0.5\ f_d$. At procedure 730, the residual polarization can be measured. The measurement can be plotted (e.g., as a Z spectrum), stored for subsequent plotting, or otherwise recorded for future use at procedure 735. If additional measurements are needed at procedure 740, $f_0$ can be varied, and re-run starting at procedure 725. Once the measurements are complete, at procedure 750 the exemplary method can use the collected data to construct a $B_0$ map.

When constructing the $B_0$ map in procedure 750, it can be supposed that $f_w$, is the real water proton resonance frequency, which can be assumed to be smaller than $f_d$. Then, the Z spectrum (e.g., as constructed above) can have two local minima when $f_0$ is equal to $0.5\ f_d+f_w$ and $-0.5\ f_d+f_w$, from which $f_w$, can be extracted. The exemplary method can find these two local minima, corresponding to the direct saturation of water protons, from the Z spectrum and take the average frequency, which can constitute the $B_0$ map. Since the extraction of $f_w$, can be performed on the interpolated Z spectrum, the distance between two minima may not be exactly $f_d$. By comparing the distance between the two local minima with $f_d$, the precision for the estimated $f_w$ can be quantified.

At procedure 760, the exemplary method can extract the corrected CEST contrast. This can include shifting the Z spectrum by the average frequency obtained above. From the shifted Z spectrum, the average frequency of the two local minima should be zero. Additionally, two data points can be found from the shifted Z spectrum, satisfying the conditions laid out above, and CEST contrast can be extracted by comparing the data values. At this point, both the $B_0$ map and CEST contrast have been created, and the exemplary method can output, record, or otherwise store the result, and terminate.

Figure 8:
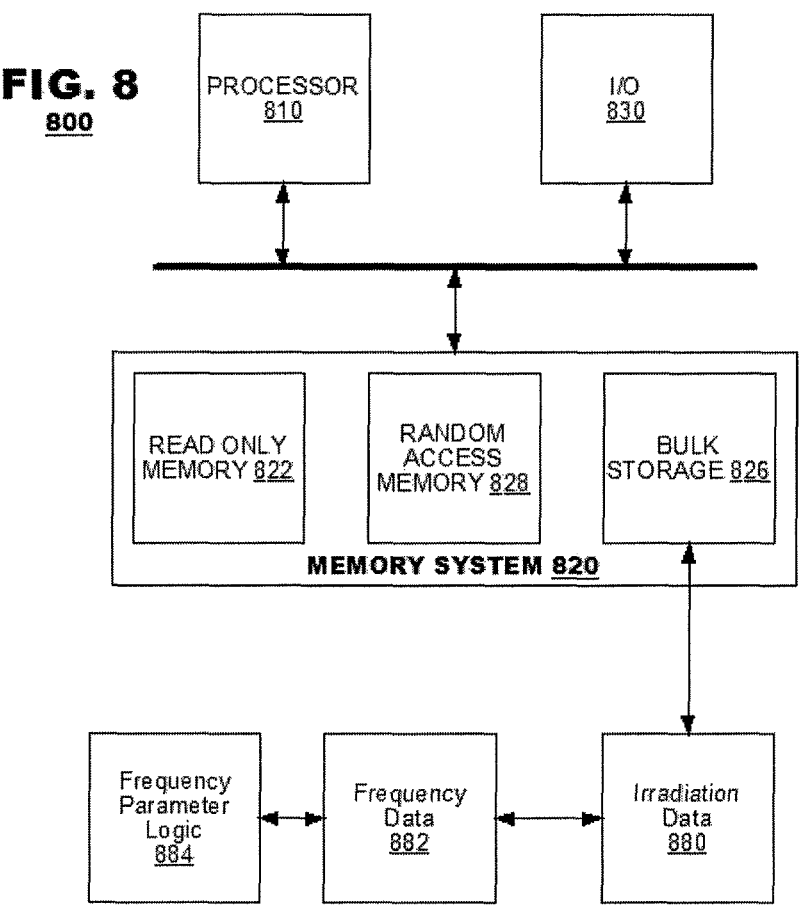
FIG. 8 is an exemplary system diagram according to exemplary embodiments of the present disclosure.

FIG. 8 illustrates an exemplary system 800 configured to execute exemplary procedures, according to other exemplary embodiments of the present disclosure. The exemplary system 800 can include a processor 810, an input/output port 830, and various memories 820, including read only memory 822, random access memory 828, and bulk storage memory 826 (e.g., a disk drive, network drive, database, etc.) Irradiation data 880 can be stored in memory, such as measured data collected from irradiation actions. Frequency data 882 can be stored in memory. Additionally, one or more parameters for frequency logic can be stored in memory 884. Exemplary system 800 can include any number of other devices or memory data.

Figure 9:
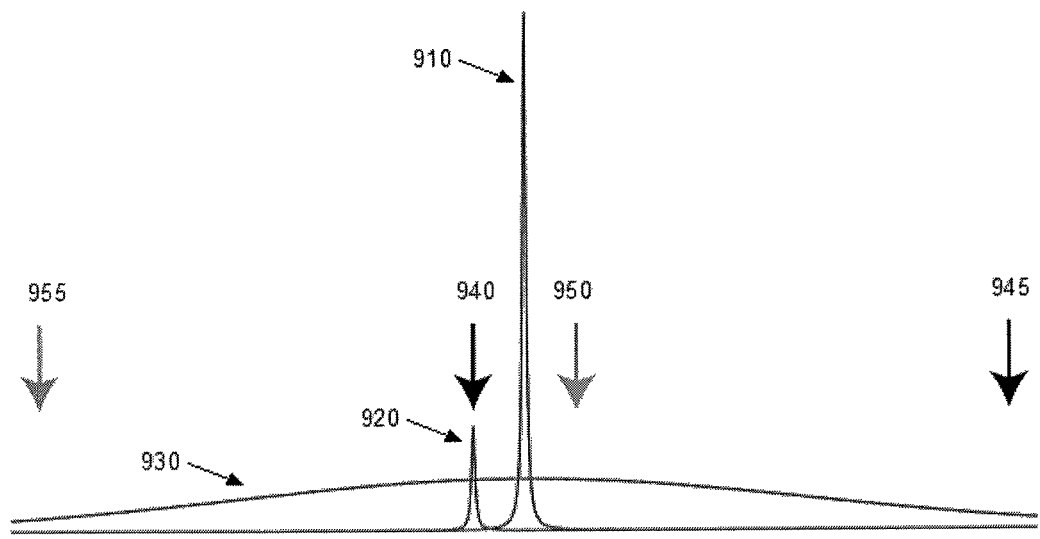
FIG. 9 is an exemplary graph describing an exemplary embodiment of the present disclosure.

FIG. 9 illustrates exemplary graphical data showing where exemplary frequency selections can be made for various exemplary embodiments of the present disclosure. Line 910 can illustrate a solution (e.g., water proton) resonance peak. Line 920 can illustrate the resonance peak of a CEST agent. Line 930 can illustrate the range of the spectrum of protons contributing magnetization transfer effects. The exemplary systems, methods and computer-readable mediums can run a first experiment using two frequencies. The first frequency 940 can be set at the resonance frequency of the CEST agent. The second frequency 945 can be chosen to be outside the typical range of spins (e.g., proton chemical shifts), and still within the range of the spectrum of protons causing magnetization transfer effects. Next, in a second experiment, a third frequency 950 can be selected symmetric to 940 about the solution resonance frequency 910 (e.g., a water proton resonance). A fourth frequency 955 can be selected symmetric to 945 about the solution resonance frequency 910. The results can be used to isolate a chemical exchange saturation transfer contrast by subtracting the first measurement from the second measurement.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. It should be understood that the exemplary procedures described herein can be stored on any computer accessible medium, including a hard drive, RAM, ROM, removable disks, CD-ROM, memory sticks, etc., and executed by a processing arrangement and/or computing arrangement which can be and/or include a hardware processors, microprocessor, mini, macro, mainframe, etc., including a plurality and/or combination thereof. In addition, certain terms used in the present disclosure, including the specification, drawings and numbered paragraphs thereof, can be used synonymously in certain instances, including, but not limited to, e.g., data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entireties.

[1] Wolff, S. D. et al., "Magnetization transfer contrast (MTC) and tissue water proton relaxation in vivo", Magn. Reson. Med., Volume 10, pg. 135-144 (1989).

[2] Henkelman, R. M. et al., "Magnetization transfer in MRI: a review", NMR Biomed., Volume 14, pg. 57-64 (2001).

[3] Leibfritz, D. et al., "Magnetization transfer MRS," NMR Biomed., Volume 14, pg. 65-76 (2001).

[4] Ward, K. M. et al., "A New Class of Contrast Agents for MRI Based on Proton Chemical Exchange Dependent Saturation Transfer (CEST)", J. Magn. Reson., Volume 143, pg. 79-87 (2000).

[5] Zhou, J. et al., "Chemical exchange saturation transfer imaging and spectroscopy," Prog. Nucl. Magn. Reson. Spectrosc., Volume 48, pg. 109-136 (2006).

[6] van Zijl, P. C. M. et al., "Chemical exchange saturation transfer (CEST): What is in a name and what isn't?", Magn. Reson. Med., Volume 65, pg. 927-948 (1011).

[7] Pekar, J. et al., "Perfusion imaging with compensation for asymmetric magnetization transfer effects", Magn. Reson. Med., Volume 35, pg. 70-79 (1996).

[8] Hua, J. et al., "Quantitative description of the asymmetry in magnetization transfer effects around the water resonance in the human brain", Magn. Reson. Med., Volume 58, pg. 786-793 (2007).

[9] Lee, J. S. et al., "Uniform saturation of a strongly coupled spin system by two-frequency irradiation", J. Chem. Phys., Volume 134, pg. 234504-1-234504-6 (2011).

[10] Lee, J. S. et al., "Pseudopure state of a twelve-spin system", J. Chem. Phys., Volume 122, pg. 041101-1-041101-3 (2005).

[11] Lee, J. S. et al., "Thermodynamics of adiabatic cross polarization", J. Chem. Phys., Volume 128, pg. 114504-1-041101-6 (2008).

[12] Provotorov, B. N. "Magnetic-resonance saturation in crystals", Zh. Eksperim. i Teor. Fiz., Volume 41, pg. 1582-1591 (1961).

[13] Goldman, M. "Spin Temperature and Nuclear Magnetic Resonance in Solids", Clarendon, Oxford, (1970).

[14] Ling, W., "Characterization of bovine patellar cartilage by NMR", NMR Biomed., Volume 21, pg. 289-295 (2008).

[15] Ling, W., "Assessment of glycosaminoglycan concentration in vivo by chemical exchange-dependent saturation transfer (gagCEST)", Proc. Natl. Acad. Sci. USA, Volume 105, pg. 2266-2270 (2008).

[16] Traoré, A. et al., "H NMR studies: dynamics of water in gelatin", Eur. Biophys. J., Volume 29, pg. 159-164 (2000).

[17] Henkelman, R. M., "Quantitative interpretation of magnetization transfer", Magn. Reson. Med., Volume 29, pg. 759-766 (1993).
[18] Levitt, M. H., "Spin dynamics: Basics of nuclear magnetic resonance", John Wiley & Sons, Chichester, (2001).
[19] Scheidegger, R. et al., "Amide proton transfer imaging with improved robustness to magnetic field inhomogeneity and magnetization transfer asymmetry using saturation with frequency alternating rf irradiation", Mang. Reson. Med., Volume 66, pg. 1275-1285 (2011).

What is claimed is:

1. A non-transitory computer-readable medium having stored thereon computer-executable instructions for isolating a chemical exchange saturation transfer (CEST), wherein, when a computer hardware arrangement executes the instructions, the computer arrangement is configured to perform procedures comprising:
determining a first frequency based on a resonance frequency of a CEST agent and a second frequency that is outside a typical range of chemical shifts for observed nuclear spins;
determining at least one of a main solvent or a medium for a sample;
causing an irradiation on the sample with both the first and second frequencies using a magnetic resonance (MR) apparatus;
receiving first data based on a first residual polarization of the irradiation of the sample with both the first and second frequencies;
determining third and fourth frequencies that are located symmetrically to the first and second frequencies, respectively, based on a resonance frequency of the at least one of the main solvent or the medium, wherein the at least one of the main solvent or the medium includes a molecule with an exchangeable nuclei;
causing an irradiation of the sample with both the third and fourth frequencies using the MR apparatus;
receiving second data based on a second residual polarization of the irradiation of the sample with both the third and fourth frequencies; and
determining third data related to a CEST contrast by subtracting the first data from the second data.

2. The computer-readable medium of claim 1, wherein the second frequency is more than about 5 parts per million away from the at least one of the main solvent or the medium.

3. The computer-readable medium of claim 1, wherein the second frequency causes magnetization transfer (MT) effects such that spins causing MT experience substantially simultaneous saturation by two frequencies.

4. The computer-readable medium of claim 3, wherein the MT effects are uniform over a frequency range.

5. The computer-readable medium of claim 4, wherein MT effects are used as an image contrast mechanism.

6. The computer-readable medium of claim 5, wherein the image contrast mechanism is robust against B0 and B1 inhomogeneities.

7. The computer-readable medium of claim 1, wherein the third and fourth frequencies are located substantially away from the first and second frequencies.

8. The computer-readable medium of claim 7, wherein the third and fourth frequencies are within a range of a spectrum of spins causing MT effects such that the spins experience substantially simultaneous saturation by the third and fourth frequencies.

9. The computer-readable medium of claim 1, wherein the subtracting of the first data from the second data reduces or eliminates a contribution of one of at least a direct solvent or medium saturation due to a pair-wise symmetric configuration.

10. The computer-readable medium of claim 1, wherein subtracting eliminates an MT contribution.

11. The computer-readable medium of claim 1, further comprising:
determining at least one further frequency;
receiving further data based on at least one further residual polarization of at least one further irradiation of the sample with the at least one further frequency; and
refining the CEST contrast by separating different exchange mechanisms.

12. The computer-readable medium of claim 1, wherein the at least one of the main solvent or the medium is at least one of water or alcohol.

13. A non-transitory computer-readable medium having stored thereon computer-executable instructions for removing Magnetization (MT) asymmetry and correcting magnetic field (B0) inhomogeneity, wherein, when a computer hardware arrangement executes the instructions, the computer arrangement is configured to perform procedures comprising:
determining a first frequency based on a resonance frequency of a chemical exchange saturation transfer (CEST) agent and a second frequency that is outside a typical range of chemical shifts for observed nuclear spins;
causing an irradiation on a sample with (i) a fourth frequency corresponding to a difference $f_d$ between the first frequency and the second frequency, and (ii) a third frequency, equal to a half sum $f_0$ of the first frequency and the second frequency using a magnetic resonance apparatus;
receiving first data based on a irradiation of the sample; and
determining second data based on a residual polarization of the first data.

14. The computer-readable medium of claim 13, wherein values of the third and fourth frequency values are measured with respect to at least one of a solvent or a medium nuclear spin resonance frequency.

15. The computer-readable medium of claim 13, further comprising:
modifying $f_0$ to a new value f1 within about $-f_d$ and $f_d$;
receiving third data based on at least one further simultaneous irradiation with frequencies based on f1; and
generating visual information associated with the residual polarization against $f_0$.

16. The computer-readable medium of claim 15, further comprising constructing a B0 map.

17. The computer-readable medium of claim 16, further comprising identifying two local minima on a plot corresponding to direct saturation of at least one of a main solvent or a medium nuclear spin resonance frequency, and averaging two frequencies respectively at the two local minima.

18. The computer-readable medium of claim 17, further comprising quantifying a precision estimate for at least one of the main solvent or the medium nuclear spin resonance frequency as $f_d$ minus an average of the two frequencies respectively at the two local minima.

19. The computer-readable medium of claim 18, further comprising correcting a CEST contrast, including shifting the plot by the average of the two frequencies respectively at the two local minima to center on zero.

20. A method for isolating a chemical exchange saturation transfer (CEST):
  determining a first frequency based on a resonance frequency of a CEST agent and a second frequency that is outside a typical range of chemical shifts for observed nuclear spins;
  determining at least one of a main solvent or a medium for a sample;
  irradiating the sample with both the first and second frequencies using a magnetic resonance (MR) apparatus;
  receiving first data based on a first residual polarization of the irradiation of the sample with both the first and second frequencies;
  determining third and fourth frequencies that are located symmetrically to the first and second frequencies, respectively, based on a resonance frequency of the at least one of the main solvent or the medium, wherein the at least one of the main solvent or the medium includes a molecule with an exchangeable nuclei;
  irradiating the sample with both the third and fourth frequencies using the MR apparatus receiving second data based on a second residual polarization of the irradiation of the sample with both the third and fourth frequencies; and
  using a computer hardware arrangement, determining third data related to a CEST contrast by subtracting the first data from the second data.

21. The method of claim 20, wherein the at least one of the main solvent or the medium is at least one of water or alcohol.

22. A system for substantially isolating a chemical exchange saturation transfer (CEST), comprising:
  a hardware processing arrangement configured to:
    determine a first frequency based on a resonance frequency of a CEST agent and a second frequency that is outside a typical range of chemical shifts for observed nuclear spins;
    determine at least one of a main solvent or a medium for a sample;
    cause an irradiation of the sample with both the first and second frequencies using a magnetic resonance (MR) apparatus;
    receive first data based on a first residual polarization of the irradiation of the sample with both the first and second frequencies;
    determine third and fourth frequencies that are located symmetrically to the first and second frequencies, respectively, based on a resonance frequency of the at least one of the main solvent or the medium, wherein the at least one of the main solvent or the medium includes a molecule with an exchangeable nuclei;
    causing an irradiation of the sample with both the third and fourth frequencies using the MR apparatus;
    receive second data based on a second residual polarization of the irradiation of the sample with both the third and fourth frequencies; and
    determine third data related to a CEST contrast by subtracting the first data from the second data.

23. The system of claim 22, wherein the at least one of the main solvent or the medium is at least one of water or alcohol.

24. A non-transitory computer-readable medium having stored thereon computer-executable instructions for isolating a first transfer in a first frequency spectrum from a second transfer in a second frequency spectrum, wherein, when a computer hardware arrangement executes the instructions, the computer arrangement is configured to perform procedures comprising:
  determining a first frequency based on a resonance frequency of a chemical exchange saturation CEST agent and a second frequency that is outside a typical range of chemical shifts for observed nuclear spins;
  determining at least one of a main solvent or a medium for a sample;
  causing a substantially-simultaneous irradiation of the sample with both the first and second frequencies using a magnetic resonance (MR) apparatus;
  receiving first data based on a first residual polarization of the substantially-simultaneous irradiation of the sample with both the first and second frequencies;
  determining third and fourth frequencies based on the first and second frequencies and a resonance frequency of the at least one of the main solvent or the medium, wherein the at least one of the main solvent or the medium includes a molecule with an exchangeable nuclei;
  causing an irradiation on the sample with both the third and fourth frequencies using the MR apparatus;
  receiving second data based on a second residual polarization of the irradiation of the sample with both the third and fourth frequencies; and
  determining third data related to substantially isolating the first transfer in the first frequency spectrum from a second transfer in a second frequency spectrum by subtracting the first data from the second data, wherein the subtraction approximately eliminates the second transfer contribution because the substantially simultaneous two-frequency irradiation makes the MT effects uniform.

25. The computer-readable medium of claim 24, wherein the first transfer is based on a first transfer mechanism and is at least one of (i) CEST in the case of chemical exchange, or (ii) Nuclear Overhauser Effect ("NOE") in the case of through-space magnetization transfer to a small mobile molecule.

26. The computer-readable medium of claim 25, wherein the second transfer is based on a second transfer mechanism where a second frequency spectrum is broader than a first frequency spectrum and is broadened by dipolar coupling including at least one of (i) magnetization transfer (MT) in the case of exchange with a bound state to a macromolecule, or (ii) magnetization transfer through space to bound moieties on the macromolecule.

27. The computer-readable medium of claim 24, wherein the first frequency is further based on a resonance frequency of the first transfer mechanism.

28. The computer-readable medium of claim 24, wherein the second frequency is more than about 5 parts per million away from the at least one of the main solvent or the medium.

29. The computer-readable medium of claim 24, wherein the second frequency causes the second transfer mechanism, such that spins causing the second transfer experience substantially simultaneous saturation by two frequencies.

30. The computer-readable medium of claim 24, wherein the third and fourth frequencies are located substantially away from the first and second frequencies.

31. The computer-readable medium of claim 24, wherein the third and fourth frequencies are within a range of a spectrum of spins causing the second transfer mechanism, such that those spins experience substantially simultaneous saturation by the third and fourth frequencies.

32. The computer-readable medium of claim 24, wherein the subtraction approximately eliminates a contribution of direct solvent or medium saturation, due to a pair-wise symmetric configuration.

33. The computer-readable medium of claim 24, wherein the at least one of the main solvent or the medium is at least one of water or alcohol.

34. A non-transitory computer-readable medium having stored thereon computer-executable instructions for isolating a chemical exchange saturation transfer (CEST), wherein, when a computer hardware arrangement executes the instructions, the computer arrangement is configured to perform procedures comprising:
   determining first and second frequencies wherein the second frequency causes magnetization transfer (MT) effects such that spins causing MT experience substantially simultaneous saturation by two frequencies;
   causing a simultaneous irradiation of a sample with both the first and second frequencies using a magnetic resonance (MR) apparatus;
   receiving first data based on a first residual polarization of the simultaneous irradiation of the sample with both the first and second frequencies;
   determining third and fourth frequencies based on the first and second frequencies;
   causing an irradiation of the sample with both the third and fourth frequencies using the MR apparatus;
   receiving second data based on a second residual polarization of the irradiation of the sample with the third and fourth frequencies; and
   determining third data related to a chemical exchange saturation transfer contrast based on the first data and the second data.

35. The computer-readable medium of claim 34, wherein the MT effects are uniform over a frequency range.

36. The computer-readable medium of claim 35, wherein the MT effects are used as an image contrast mechanism.

37. The computer-readable medium of claim 36, wherein the image contrast mechanism is robust against B0 and B1 inhomogeneities.

* * * * *

UNITED STATES PATENT AND TRADEMARK OFFICE
CERTIFICATE OF CORRECTION

PATENT NO. : 9,709,511 B2
APPLICATION NO. : 13/687342
DATED : July 18, 2017
INVENTOR(S) : Jae Seung Lee et al.

Page 1 of 1

It is certified that error appears in the above-identified patent and that said Letters Patent is hereby corrected as shown below:

In the Specification

The second paragraph under Column 1, Line 20, delete the paragraph and insert the following:
-- STATEMENT REGARDING FEDERALLY SPONSORED RESEARCH
This invention was made with government support under grant number(s) K25AR060269 and R21AR055724 awarded by the National Institutes of Health and under grant number CHE0957586 awarded by the National Science Foundation. The government has certain rights in this invention. --

Signed and Sealed this
Thirty-first Day of July, 2018

Andrei Iancu
*Director of the United States Patent and Trademark Office*